US011382635B2

(12) United States Patent
Inouye et al.

(10) Patent No.: US 11,382,635 B2
(45) Date of Patent: Jul. 12, 2022

(54) OCCLUSIVE MEDICAL DEVICE

(71) Applicant: BOSTON SCIENTIFIC SCIMED, INC., Maple Grove, MN (US)

(72) Inventors: Joshua Mark Inouye, Maple Grove, MN (US); David John Onushko, Minneapolis, MN (US); Dennis A. Peiffer, Brooklyn Park, MN (US); James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 190 days.

(21) Appl. No.: 16/502,190

(22) Filed: Jul. 3, 2019

(65) Prior Publication Data
US 2020/0008812 A1 Jan. 9, 2020

Related U.S. Application Data

(60) Provisional application No. 62/694,731, filed on Jul. 6, 2018.

(51) Int. Cl.
*A61B 17/12* (2006.01)
*A61B 17/00* (2006.01)

(52) U.S. Cl.
CPC .. *A61B 17/12122* (2013.01); *A61B 17/12172* (2013.01); *A61B 2017/00526* (2013.01); *A61B 2017/00579* (2013.01); *A61B 2017/00632* (2013.01); *A61B 2017/00867* (2013.01)

(58) Field of Classification Search
CPC ...... A61F 2/01; A61F 2/013; A61F 2002/011; A61B 17/12122; A61B 17/12172; A61B 2017/00526; A61B 17/12
See application file for complete search history.

(56) References Cited

U.S. PATENT DOCUMENTS

| 1,782,830 | A | 6/1876 | French |
| 1,967,318 | A | 10/1931 | Monahan |
| 3,402,710 | A | 9/1968 | Paleschuck |

(Continued)

FOREIGN PATENT DOCUMENTS

| CN | 106859722 A | 6/2017 |
| EP | 3311782 A1 | 4/2018 |

(Continued)

OTHER PUBLICATIONS

International Search Report and Written Opinion dated Oct. 16, 2019 for International Application No. PCT/US2019/040502.

(Continued)

*Primary Examiner* — Vi X Nguyen
(74) *Attorney, Agent, or Firm* — Seager, Tufte & Wickhem LLP

(57) ABSTRACT

An example occlusive implant is disclosed. The example occlusive implant includes an expandable framework configured to shift between a first configuration and an expanded configuration and a fixation member disposed along the expandable framework. The fixation member includes a first engagement portion and an anchor portion. Further, the first engagement portion is designed to be secured to the expandable framework and the anchor portion extends away from an outer surface of the expandable framework.

10 Claims, 17 Drawing Sheets

(56) References Cited

U.S. PATENT DOCUMENTS

| | | |
|---|---|---|
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |

(56) References Cited

U.S. PATENT DOCUMENTS

| | | | |
|---|---|---|---|
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 * | 5/2001 | Frazier ............. A61B 17/12122 604/500 |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Knya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 | 1/2005 | Rabkin et al. |
| 6,855,153 B2 | 2/2005 | Saadat |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 8,062,282 B2 | 11/2011 | Kolb |
| 8,491,623 B2 | 7/2013 | Vogel et al. |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0082638 A1 | 6/2002 | Porter et al. |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0181942 A1 | 9/2003 | Sutton et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2013/0007302 A1 | 3/2013 | Shaw |
| 2013/0013171 A1 | 5/2013 | Glimsdale |
| 2014/0005714 A1 * | 1/2014 | Quick ............... A61B 17/12031 606/200 |
| 2014/0039536 A1 | 2/2014 | Cully et al. |
| 2014/0100596 A1 | 4/2014 | Rudman et al. |
| 2014/0142610 A1 | 5/2014 | Larsen et al. |
| 2014/0188157 A1 | 7/2014 | Clark |
| 2014/0336612 A1 | 11/2014 | Frydlewski et al. |
| 2015/0005809 A1 | 1/2015 | Ayres et al. |
| 2016/0106437 A1 | 4/2016 | Van Der Burg et al. |
| 2016/0287259 A1 | 10/2016 | Hanson et al. |
| 2018/0125682 A1 | 5/2018 | Folan et al. |
| 2019/0223883 A1 | 7/2019 | Anderson et al. |

FOREIGN PATENT DOCUMENTS

| | | |
|---|---|---|
| GB | 2491483 A | 12/2012 |
| WO | 9313712 A1 | 7/1993 |
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2013159065 A1 | 10/2013 |
| WO | 2015164836 A1 | 10/2015 |
| WO | 20170161283 A1 | 9/2017 |
| WO | 2018017935 A1 | 1/2018 |
| WO | 2018187732 A1 | 10/2018 |

OTHER PUBLICATIONS

PCT Search Report from co-pending Application PCT/US02/33808 dated May 20, 2003.

PCT Search Report from PCT/US99/26325 dated Feb. 15, 2000.

Cragg et al; "Nonsurgical Placement of Arterial Endoprosthesis: A New Technique Using Nitinol Wire," Radiology vol. 147, No. 1 pp. 261-263, Apr. 1983.

Cragg et al; "A New Percutaneous Vena Cava Filter", ALJ, 141: 601-604, Sep. 1983.

(56) References Cited

OTHER PUBLICATIONS

Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; Nonsurgical Closure of Patent Ductus Arteriosus: Clinical Application of the Rashkind PDA Occluder System, Circulation 75, No. 3, 583-592-1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.
International Search Report and Written Opinion dated Sep. 9, 2019 for International Application No. PCT/US2019/033698.

\* cited by examiner

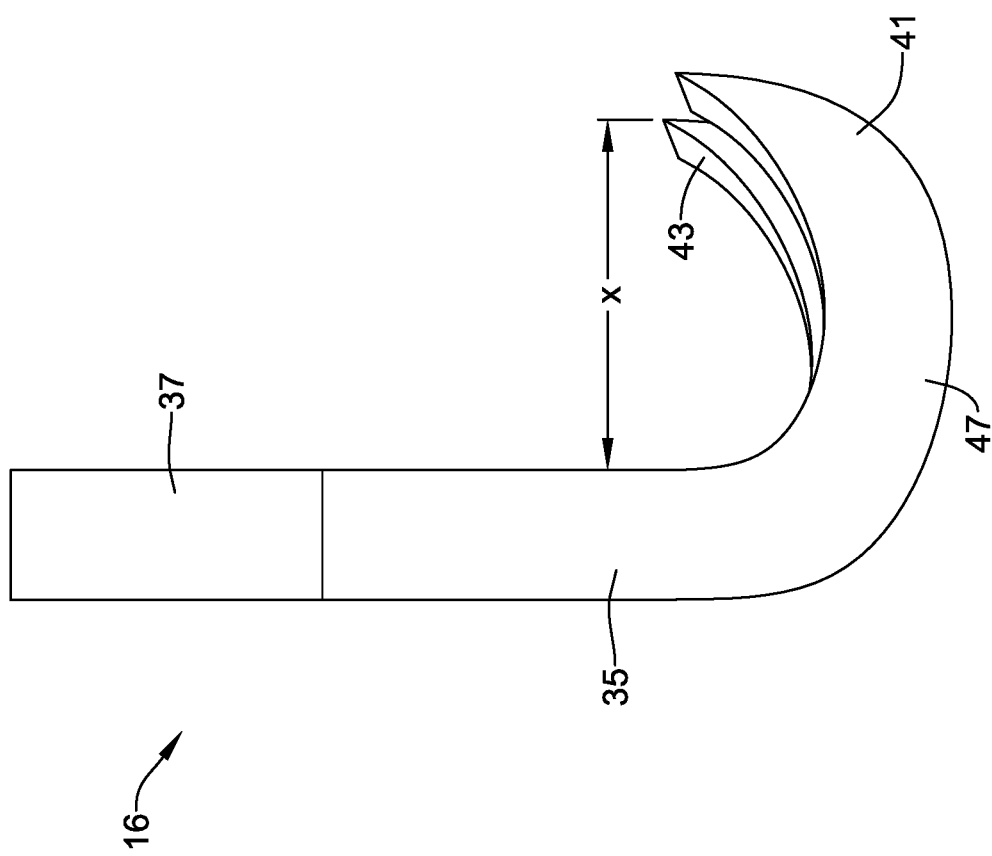

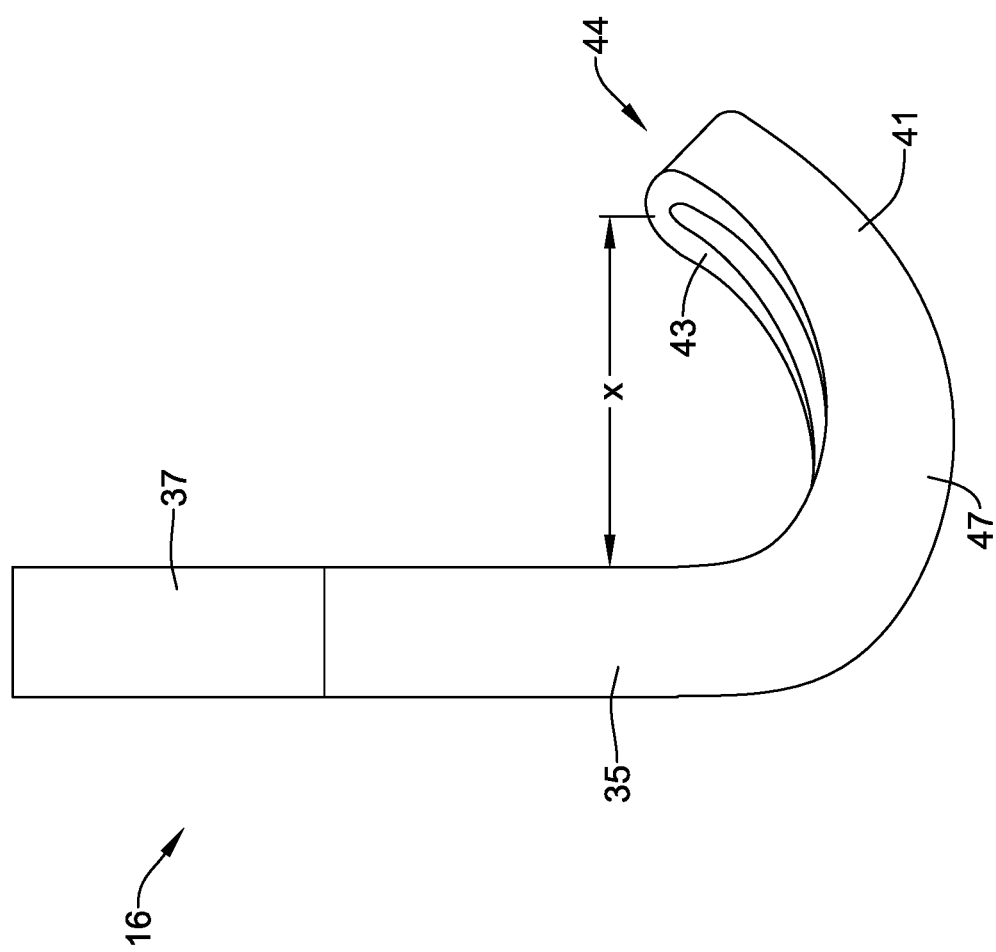

OCCLUSIVE MEDICAL DEVICE

CROSS-REFERENCE TO RELATED APPLICATIONS

This application claims the benefit of priority under 35 U.S.C. § 119 to U.S. Provisional Application Ser. No. 62/694,731, filed Jul. 6, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example occlusive implant includes an expandable framework configured to shift between a first configuration and an expanded configuration and a fixation member disposed along the expandable framework. The fixation member includes a first engagement portion and an anchor portion. Further, the first engagement portion is designed to be secured to the expandable framework and the anchor portion extends away from an outer surface of the expandable framework.

In addition or alternatively, wherein the first engagement portion is removably secured to the expandable framework.

In addition or alternatively, wherein the first engagement portion is designed to be rigidly secured to the expandable framework.

In addition or alternatively, wherein the fixation member includes a first end, a second end opposite the first end and a medial portion extending between the first end and the second end, and wherein the first engagement portion is positioned along the first end of the fixation member and wherein the anchor portion is positioned along the second end of the fixation member.

In addition or alternatively, wherein the first engagement portion includes a first engagement member and a second engagement member, wherein both the first engagement member and the second engagement member are offset from the medial portion.

In addition or alternatively, wherein at least a portion of the expandable framework is positioned between the first engagement member and the medial portion and wherein at least a portion of the expandable framework is positioned between the second engagement member and the medial portion.

In addition or alternatively, wherein the fixation member is disposed along the expandable framework such that at least a portion of first engagement member and at least a portion of the second engagement member are positioned along an outer surface of the expandable framework and at least a portion of the medial portion is positioned along an inner surface of the expandable framework.

In addition or alternatively, wherein the expandable framework includes a first filament interwoven with a second filament, and wherein the first filament crosses the second filament at an intersection point, and wherein the fixation member is positioned adjacent to the intersection point.

In addition or alternatively, wherein the first filament is positioned between the first engagement member and the medial portion, and wherein the second filament is positioned between the second engagement member and the medial portion.

In addition or alternatively, wherein the anchor portion includes a first projection and a second projection, and wherein the second projection is offset from the first projection.

In addition or alternatively, wherein each of the first projection and the second projection includes an arcuate portion.

In addition or alternatively, wherein the fixation portion further comprises a second engagement portion positioned adjacent to the first engagement portion, and wherein the second engagement portion includes a third engagement member and a fourth engagement member.

In addition or alternatively, wherein the fixation member is disposed along the expandable framework such that at least a portion of third engagement member and at least a portion of the fourth engagement member are positioned along the outer surface of the expandable framework and at least a portion of the medial portion is positioned along the inner surface of the expandable framework.

In addition or alternatively, wherein at least one of the first engagement member, the second engagement member, the third engagement member and the fourth engagement member are interlaced with a least a portion of the expandable framework.

A method of manufacturing an occlusive device within the left atrial appendage includes:

securing a fixation member to an expandable framework, wherein the fixation member includes a first engagement portion, a medial portion and an anchor portion, and wherein the expandable framework is configured to shift between a first configuration and an expanded configuration;

wherein the anchor portion extends away from an outer surface of the expandable framework.

In addition or alternatively, wherein securing the fixation member to the expandable framework includes attaching the fixation member via frictional fixation.

In addition or alternatively, wherein attaching the fixation member via frictional fixation includes positing the expandable member between the first engagement portion and the medial portion.

In addition or alternatively, wherein securing the fixation member to the expandable framework includes rigidly attaching the fixation member to the expandable framework.

In addition or alternatively, wherein securing the fixation member to the expandable framework includes welding the fixation member to the expandable framework.

A method for occluding a left atrial appendage includes: advancing an occlusive implant to the left atrial appendage, the occlusive implant including:

an expandable framework configured to shift between a first configuration and a second configuration; and a fixation member disposed along the expandable framework, wherein the fixation member includes a first engagement portion and an anchor portion;

wherein the anchor portion extends away from an outer surface of the expandable framework;

wherein the first engagement portion is removably coupled to the expandable framework; and expanding the expandable framework within the left atrial appendage such that the expandable framework shifts between the first configuration and the second configuration.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 5 is a side view of the fixation member shown in FIG. 4;

FIG. 5A is a side view of another fixation member;

Figure 1:
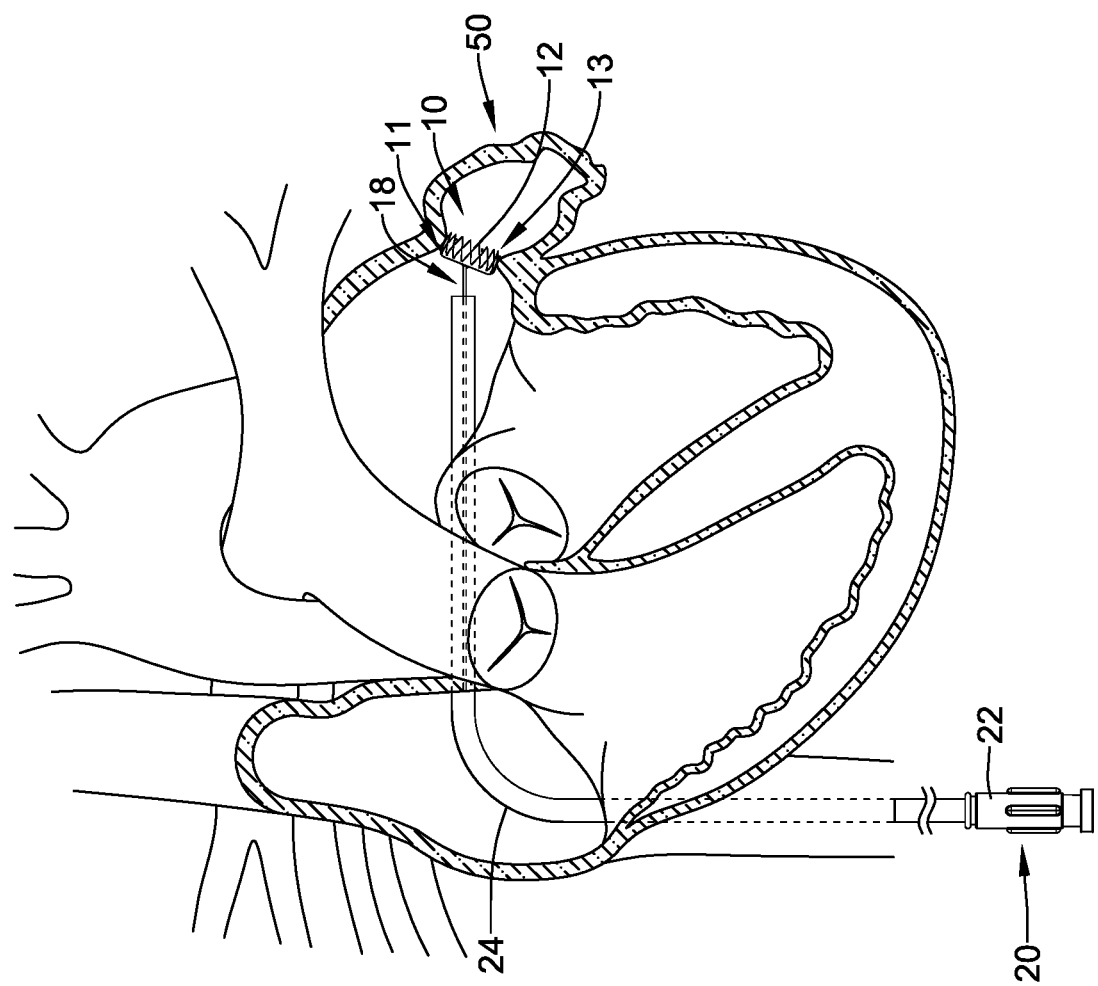
FIG. 1 illustrates an example occlusive implant positioned in the heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants which seal the left atrial appendage (or other similar openings) are disclosed herein.

FIG. 1 illustrates an example occlusive implant 10 positioned within the left atrial appendage 50. FIG. 1 further illustrates that the occlusive implant 10 may be inserted and advanced through a body lumen via an occlusive implant delivery system 20. In some instances, an occlusive implant delivery system 20 may include a delivery catheter 24 which is guided toward the left atrium via various chambers and lumens of the heart (e.g., the inferior vena cava, superior vena cava, the right atrium, etc.) to a position adjacent the left atrial appendage 50.

The delivery system 20 may include a hub 22. The hub 22 may be manipulated by a clinician to direct the distal end region of the delivery catheter 24 to a position adjacent the left atrial appendage 50. In some embodiments, an occlusive implant delivery system 20 may include a core wire 18. Further, a proximal end 11 of the occlusive implant 10 may be configured to releasably attach, join, couple, engage, or otherwise connect to the distal end of the core wire 18. In some embodiments, the proximal end region 11 of the occlusive implant 10 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the occlusive implant 10 to the distal end of the core wire 18 are also contemplated.

FIG. 1 further illustrates the occlusive implant 10 positioned adjacent the left atrial appendage 50 via the delivery catheter 24 (described above). It can be appreciated that in some examples, the implant 10 may be configured to shift between a collapsed configuration and an expanded configuration. For example, in some instances, the occlusive implant 10 may be in a collapsed configuration during delivery via the occlusion implant delivery system 20, whereby the occlusive implant 10 expands to an expanded configuration once deployed from the occlusion implant delivery system 20.

Additionally, FIG. 1 illustrates that the occlusive implant 10 may include an expandable framework 12. The expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue and/or lateral wall of the left atrial appendage 50. Further, it can be appreciated that the elements of the expandable framework 12 may be tailored to increase the flexibility of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 to include various features, components and/or configurations which improve the sealing capabilities of the occlusive implant 10 within the left atrial appendage.

FIG. 1 illustrates that the distal end region 13 of the expandable framework 12 may extend farther into the left atrial appendage 50 as compared to the proximal end region 11 of the expandable framework 12. It can be appreciated that as the expandable framework 12 is advanced into the left atrial appendage 50, the distal end region 13 may engage with tissue defining the left atrial appendage 50. In other words, in some examples the distal end region 13 may be considered the "leading" region of the expandable framework 12 as it enters into the left atrial appendage 50. However, this is not intended to be limiting. Rather, in some examples the proximal end region 11 may be considered the "leading" region of the expandable framework 12 as it enters into the left atrial appendage 50.

Figure 2:
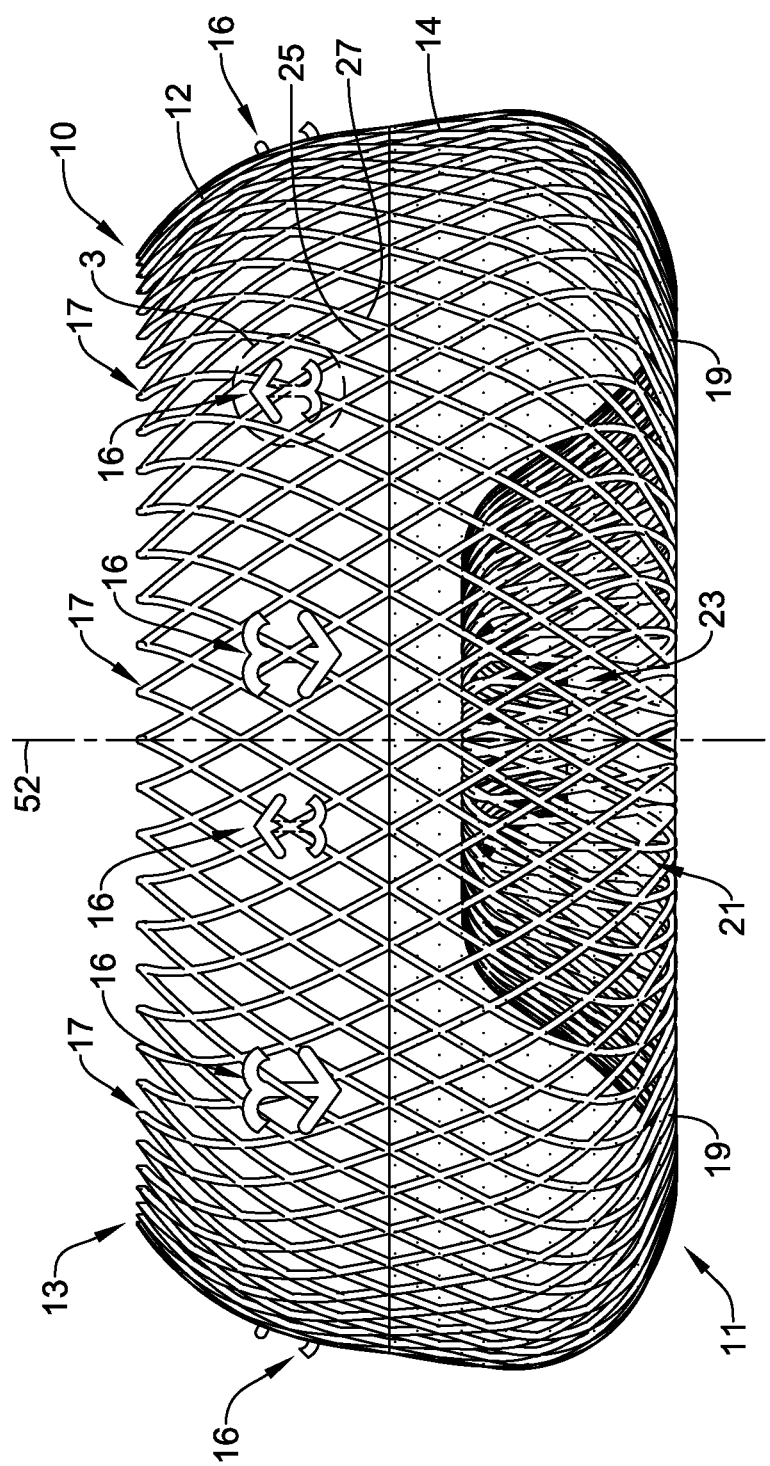
FIG. 2 is a plan view of an example occlusive implant.

FIG. 2 illustrates an example occlusive implant 10. The implant 10 may include an expandable framework 12. As illustrated in FIG. 2, in some examples the expandable framework 12 may be formed as a braided structure (e.g., a framework formed by braiding one or more filaments together). For example, the expandable framework 12 may include a first filament 25 interwoven with a second filament 27 to form a braided expandable framework 12. The expandable framework 12 may include a proximal end region 11 and a distal end region 13. FIG. 2 further illustrates that the expandable framework 12 may include one or more projections 17 extending in a proximal-to-distal direction. In some instances (such as that shown in FIG. 2), the plurality of projections 17 may extend circumferentially around a longitudinal axis 52 of the expandable framework 12. In other words, the projections 17 may resemble the peaks of a "crown" extending circumferentially around a longitudinal axis 52 of the expandable framework 12. While the above discussion (and the illustration shown in FIG. 2), shows a plurality of projections 17, it is contemplated that the occlusive implant 10 may include 1, 2, 3, 4, 5, 6, 7, 8, 9, 10, 11, 12 or more individual projections 17 disposed in a variety of arrangements along the expandable framework 12.

Additionally, FIG. 2 illustrates that the proximal end region 11 of the expandable framework 12 may include a plurality of support members 19 extending circumferentially around the longitudinal axis 52 of the expandable framework 12. FIG. 2 illustrates that the plurality of support members 19 may include one or more curved portions which are shaped such that they define a "recess" 21 extending distally into the expandable framework 12. As illustrated in FIG. 2, the recess 21 may extend circumferentially around the longitudinal axis 52. Further, FIG. 2 illustrates that each of the plurality of support members 19 may be attached to a central hub 23. It can be appreciated that the central hub 23 may be aligned along the longitudinal axis 52 of the expandable framework 12. As will be described in greater detail below, FIG. 2 illustrates that the hub 23 may be positioned such that it lies within the recess 21 defined by the plurality of support members 19.

FIG. 2 further illustrates that the expandable framework 12 may include one or more fixation members 16 disposed about a periphery of the expandable framework 12. As will be discussed in greater detail below, each of the fixation members 16 may be secured to the expandable framework 12 such that a portion of each of the fixation members 16 may extend radially outward from the outer surface of the expandable framework 12. Some suitable, but non-limiting, examples of materials for the expandable framework 12 and/or the fixation members 16 are discussed below.

Additionally, FIG. 2 illustrates that one or more of the fixation members 16 may be offset substantially 180 degrees from one or more adjacent fixation members 16. In other words, some fixation members 16 may be aligned such that they point from the proximal end region 11 to the distal end region 13, while other fixation members may be positioned such that they point from the distal end region 13 to the proximal end region 11. Further, FIG. 2 is not intended to be limiting. Rather, it is contemplated that one or more of the fixation members 16 may be aligned in a variety of different orientations along the expandable framework 12.

While FIG. 2 illustrates that the expandable framework 12 may be formed as a braided structure, this is not intended to be limiting. Rather, it is contemplated the expandable member 12 may include a variety of different configurations which may be formed via a variety of manufacturing techniques. For instance, some example occlusive implants may be integrally formed and/or cut from a unitary member. For example, in some embodiments the expandable framework 12 may be integrally formed and/or cut from a unitary tubular member and subsequently formed and/or heat set to a desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

The occlusive implant 10 may also include a first occlusive member 14 disposed on, disposed over, disposed about, or covering at least a portion of the expandable framework 12. In some embodiments, the first occlusive member 14 may be disposed on, disposed over, disposed about or cover at least a portion of an outer (or outwardly-facing) surface of the expandable framework 12. FIG. 2 further illustrates that the first occlusive member 14 may extend only partially along the longitudinal extent of the expandable framework 12. However, this is not intended to be limiting. Rather, the first occlusive member 14 may extend along the longitudinal extent of the expandable framework 12 to any degree (e.g., the full longitudinal extend of the expandable framework 12).

In some embodiments, the first occlusive member 14 may be permeable or impermeable to blood and/or other fluids, such as water. In some embodiments, the first occlusive member 14 may include a woven, braided and/or knitted material, a fiber, a sheet-like material, a fabric, a polymeric membrane, a metallic or polymeric mesh, a porous filter-like material, or other suitable construction. In some embodiments, the first occlusive member 14 may prevent thrombi (i.e. blood clots, etc.) from passing through the first occlusive member 14 and out of the left atrial appendage into the blood stream. In some embodiments, the first occlusive member 14 may promote endothelialization after implantation, thereby effectively removing the left atrial appendage from the patient's circulatory system. Some suitable, but non-limiting, examples of materials for the first occlusive member 14 are discussed below.

Figure 3:
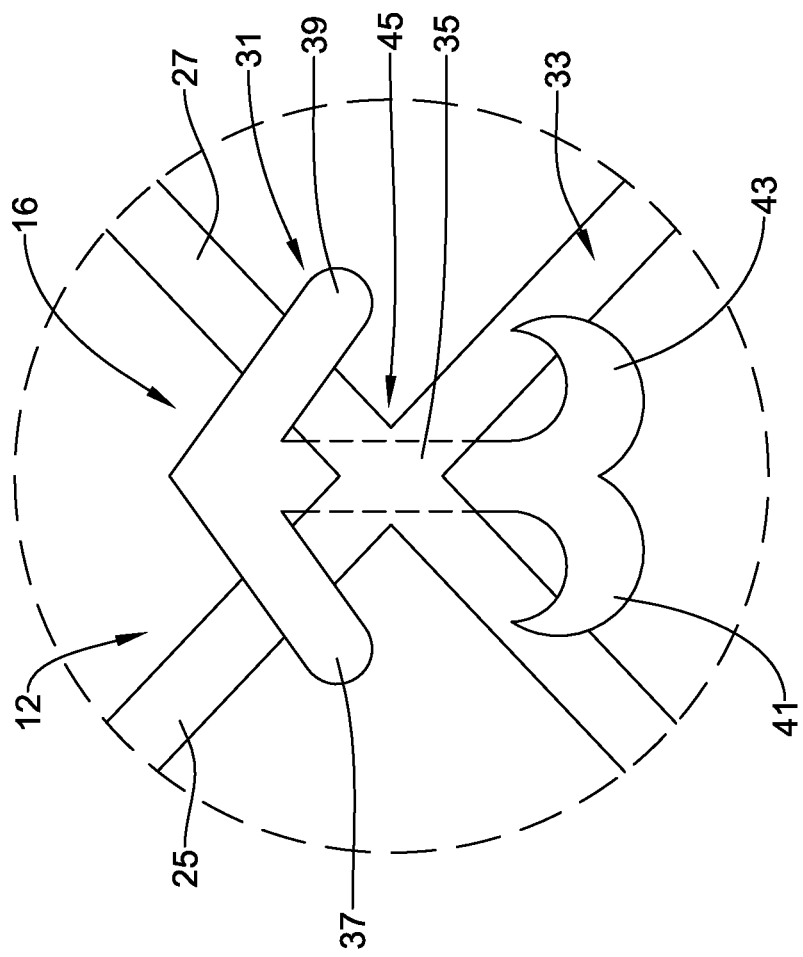
FIG. 3 illustrates an example fixation member disposed along an occlusive implant.

FIG. 3 illustrates an example fixation member 16. The example fixation member 16 may include an engagement portion 31 positioned on a first end the fixation member 16 and an anchoring portion 33 positioned on a second end of the fixation member 16. As shown in FIG. 3, the second end of the fixation member 16 may be positioned opposite to the first end of the fixation member 16. Additionally, the fixation member 16 may include a medial portion 35 extending between the engagement portion 31 and the anchoring portion 33. In other words, the medial portion 35 may span between the engagement portion 31 and the anchoring portion 33.

FIG. 3 further illustrates that the engagement portion 31 of the fixation member 16 may include a first engagement member 37 and a second engagement member 39. Each of the first engagement member 37 and the second engagement member 39 may be formed as a monolithic structure with the medial portion 35. Further, it can be appreciated from FIG. 3 that each of the first engagement member 37 and the second engagement member 39 may be offset from the medial portion 35. For example, in some instances the combination of the first engagement member 37, the second engagement member 39 and the medial portion 35 may resemble the shape of an "arrow." However, this is not intended to be limiting. Rather, the first engagement member 37 and the second engagement member 39 may be positioned relative to the medial portion 35 at a variety of angles, offsets, etc.

Additionally, FIG. 3 illustrates that, in some examples, the first engagement member 37 and/or the second engagement member 39 may cooperate with the medial portion 35 to releasably secure (e.g., couple, attach, fix, etc.) the fixation member 16 to the expandable framework 12. As shown in FIG. 3, both the first engagement member 37 and the second engagement member 39 may be positioned such that they extend along the outer surface of the expandable framework 12 while the medial portion 35 may be positioned such that it extends along the inner surface of the expandable framework 12 (it is noted that the portion of the medial portion 35 extending along the inner surface of the expandable framework 12 is depicted by the dashed lines in FIG. 3). In particular, FIG. 3 illustrates that the first engagement member 37 may extend along the first filament 25 (e.g., the first engagement member 37 may be positioned on the outer surface of the first filament 25) and the second engagement member 39 may extend along the second filament 27 (e.g., the second engagement member 39 may be positioned on the outer surface of the second filament 27). Further, FIG. 3 illustrates that the first filament 25 and the second filament 27 may cross one another at an intersection point 45, whereby the medial portion 35 may extend along the inner surface of intersection portions of the first filament 25 and the second filament 27. Therefore, it can be appreciated that positioning the first engagement member 37 and the second engagement 39 on the outer surface of the expandable member 12 and positioning the medial portion 35 along the inner surface of the expandable member 12 may permit the first filament 25 and the second filament 27 to be secured (e.g., affixed, squeezed, pinched, etc.) between the first engagement member 37, the second engagement member 39 and the medial portion 35.

It can further be appreciated that the design of the engagement portion 31 described above with respect to positioning the expandable framework 12 between the first engagement member 37, the second engagement member 39 and the medial portion 35 of the fixation member 16 may permit the fixation member 16 to be manufactured as a separate component which may be releasably fixed to the expandable member 12. For example, the fixation member 16 may be manufactured separately from the expandable framework 12, whereby the fixation member 16 may be secured to the expandable framework 12 at a later time. This manufacturing technique may be advantageous because it may improve the manufacturing efficiency of the occlusive device 10. For example, designing the occlusive device 10 to include a separately attached fixation member 16 may permit tighter manufacturing control of the fixation member 16.

FIG. 3 further illustrates that the anchoring portion 33 of the fixation member 16 may include a first projection 41 and a second projection 43 positioned along a second end of the fixation member 16 opposite the first engagement portion 31. As will be discussed in greater detail below, each of the first projection 41 and the second projection 43 may extend away from the outer surface of the expandable member 12. It can be appreciated that each of the first projection 41 and the second projection 43 may be designed to engage tissue at a target location. In other words, the first projection 41 and the second projection 43 may be designed to pierce tissue at a target site, thereby securing the position of an occlusive device adjacent the target site (e.g., the left atrial appendage).

Figure 4:
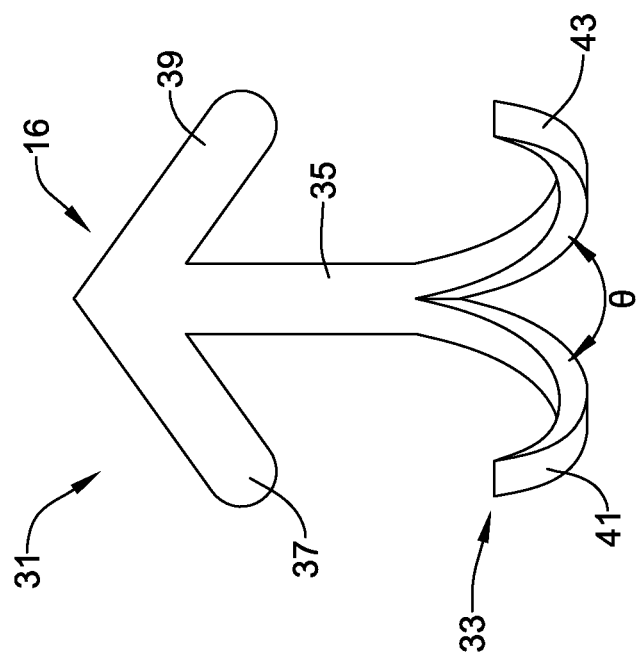
FIG. 4 is a perspective view of the fixation member shown in FIG. 3.

FIG. 4 is a perspective view of the fixation member 16 discussed above with respect to FIG. 2 and FIG. 3. As described above, FIG. 4 illustrates that the fixation member 16 may include a first engagement portion 31 including the first engagement member 37 and a second engagement member 39. Additionally, FIG. 4 illustrates that the fixation member 16 may include an anchoring portion 33 which includes the first projection 41 and the second projection 43. Further, FIG. 4 illustrates the medial portion 35 extending between the engagement portion 31 and the anchoring portion 33.

As will be illustrated in greater detail with respect to FIG. 5, the first projection 41 and/or the second projection 43 may include a curved portion which extends the distal ends of the first projection 41 and the second projection 43 outward from the medial portion 35 of the fixation member 16. For example, FIG. 4 illustrates the first projection 41 and the second projection 43 extending outward from the plane of the paper. Additionally, FIG. 4 illustrates that the first projection 41 may be separated from the second projection 43. In other words, FIG. 4 illustrates that the first projection 41 and the second projection 43 may be separated from one another by an angle "θ."

FIG. 5 shows a side view of the fixation member 16. Specifically, FIG. 5 illustrates that each of the first projection 41 and the second projection 43 may include an arcuate portion 47. As discussed above, the arcuate portion 47 may be configured to extend the distal end of each of the first projection 41 and the second projection 43 away from the medical portion 35 a distance "X." Additionally, it can be appreciated that the arcuate portion 47 may be configured to pierce and embed within tissue of a target site (e.g., the left atrial appendage).

FIG. 5A illustrates another example of the fixation member 16 shown in FIG. 5 whereby the distal ends of the first projection 41 and the second projection 43 are connected to form an atraumatic projection 44. As illustrated in FIG. 5A, the distal ends of the first projection 41, the second projection 43 or both the first projection 41 and the second projection 43 may extend in a curved manner to form a continuous, curved atraumatic distal end 44. It can be appreciated that the atraumatic distal end 44 may permit the fixation member 16 to provide mechanical fixation by engaging target tissue without puncturing the tissue.

Figure 6:
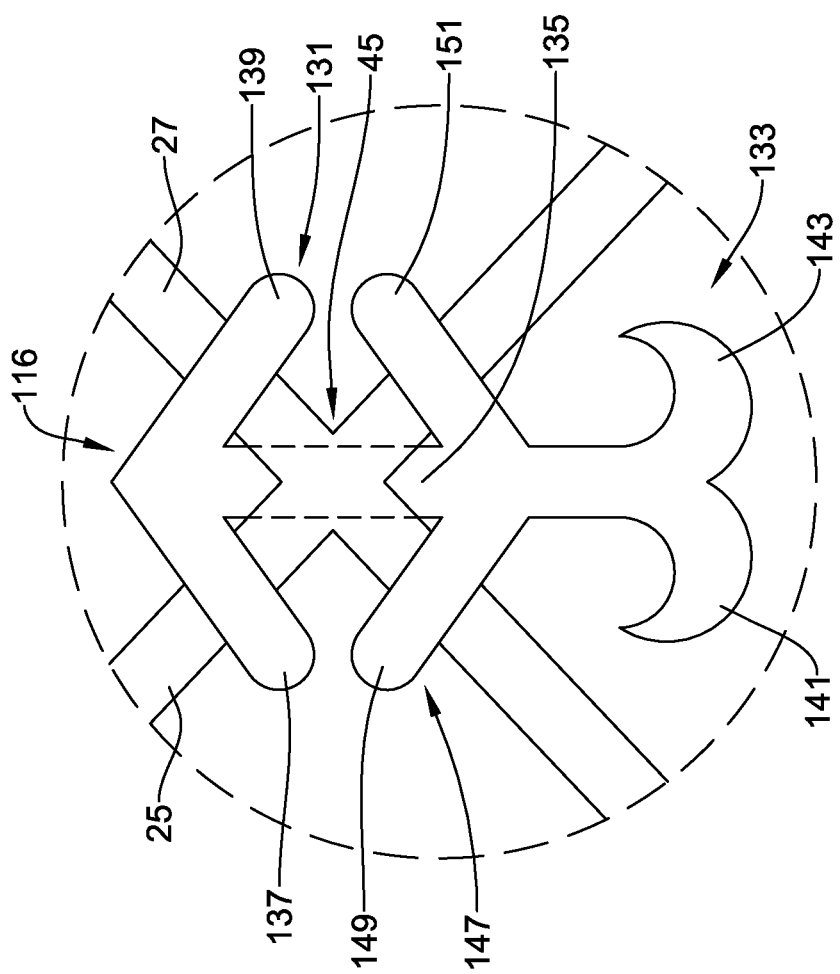
FIG. 6 illustrates another example fixation member disposed along an occlusive implant.

FIG. 6 illustrates another example fixation member 116. The fixation member 116 may be similar in form and function to other example fixation members described herein. For example, the example fixation member 116 may include an engagement portion 131 positioned on a first end of the fixation member 116 and an anchoring portion 133 positioned on a second end of the fixation member 116. The second end of the fixation member 116 may be positioned opposite to the first end of the fixation member 116. Additionally, the fixation member 116 may include a medial portion 135 which may extend between the engagement portion 131 and the anchoring portion 133.

FIG. 6 further illustrates that the engagement portion 131 of the fixation member 116 may include a first engagement member 137 and a second engagement member 139. Each of the first engagement member 137 and the second engagement member 139 may be formed as a monolithic structure with the medial portion 135. Further, it can be appreciated from FIG. 6 that each of the first engagement member 137 and the second engagement member 139 may be offset from the medial portion 135 at an angle. However, it is contemplated that the first engagement member 137 and the second engagement member 139 may be positioned relative to the medial portion 135 at a variety of angles, offsets, etc.

Similar to that described above with respect to FIG. 3, FIG. 6 further illustrates that the first engagement member 137 may extend along the first filament 25 (e.g., the first engagement member 137 may be positioned on the outer surface of the first filament 25) and the second engagement member 139 may extend along the second filament 27 (e.g., the second engagement member 39 be positioned on the outer surface of the second filament 27). Further, FIG. 6 illustrates that the first filament 25 and the second filament 27 may cross one another at the intersection point 45, whereby the medial portion 135 may extend along the inner surface of the both the first filament 25 and the second filament 27 (it is noted that the portion of the medial portion 35 extending along the inner surface of the expandable framework 12 is depicted by the dashed lines in FIG. 6).

As described above, FIG. 6 further illustrates that the anchoring portion 133 of the fixation member 116 may include a first projection 141 and a second projection 143 positioned along a second end of the fixation member 116 opposite the first end of the fixation member 116. As will be discussed in greater detail below, each of the first projection 141 and the second projection 143 may extend away from the outer surface of the expandable member 112. It can be appreciated that each of the first projection 141 and the second projection 143 may be designed to engage tissue at a target location. In other words, the first projection 141 and the second projection 143 may be designed to pierce into tissue at a target site, thereby securing the position of an occlusive device adjacent the target site (e.g., the left atrial appendage).

FIG. 6 further illustrates that the example fixation member 116 may include a second engagement portion 147. The second engagement portion 147 may be positioned adjacent to the first engagement portion 131. Additionally, the second engagement portion may include a third engagement member 149 and a fourth engagement member 151. Each of the third engagement member 149 and the fourth engagement member 151 may be formed as a monolithic structure with the medial portion 135. Further, it can be appreciated from FIG. 6 that each of the third engagement member 149 and the fourth engagement member 151 may be offset from the medial portion 135. Additionally, FIG. 6 illustrates that the third engagement member 149 and the fourth engagement member 151 may be positioned such that they are angled substantially toward the first engagement member 137 and the second engagement member 139. However, it is contemplated that the third engagement member 149 and the fourth engagement member 151 may be oriented relative to the medial portion 135 and/or the first engagement member 137 and second engagement member 139 at a variety of angles, offsets, etc.

Additionally, FIG. 6 further illustrates that the third engagement member 149 may extend along the second filament 27 (e.g., the third engagement member 149 may be positioned on the outer surface of the second filament 27) and the fourth engagement member 151 may extend along the first filament 25 (e.g., the fourth engagement member 151 be positioned on the outer surface of the first filament 25). Further, FIG. 6 illustrates that the first filament 25 and the second filament 27 may cross one another at the intersection point 45, whereby the medial portion 135 may extend along the inner surface of the both the first filament 25 and the second filament 27.

Similar to that described above, the second engagement portion 147 may cooperate with the first engagement portion 131 to secure the fixation member 116 to the expandable framework 12. In particular, the third engagement member 149 and the fourth engagement member 151 may cooperate with the medial portion 135 of the fixation member 116 to secure (e.g., couple, attach, fix, etc.) the fixation member 116 to the expandable framework 12. As shown in FIG. 6, both the third engagement member 149 and the fourth engagement member 151 may be positioned such that they extend along the outer surface of the first filament 25 and the second filament 27, while the medial portion 135 may be positioned such that it extends along the inner surface of the expandable framework 12. Therefore, it can be appreciated that positioning the third engagement member 149 and the fourth engagement member 151 on the outer surface of the expandable member 12 and positioning the medial portion 135 along the inner surface of the expandable member 12 may permit the first filament 25 and the second filament 27 to be positioned (e.g., affixed, squeezed, pinched, etc.) between the first engagement member 137, the second engagement member 139, the third engagement member 149, the fourth engagement member 151 and the medial portion 35.

Figure 7:
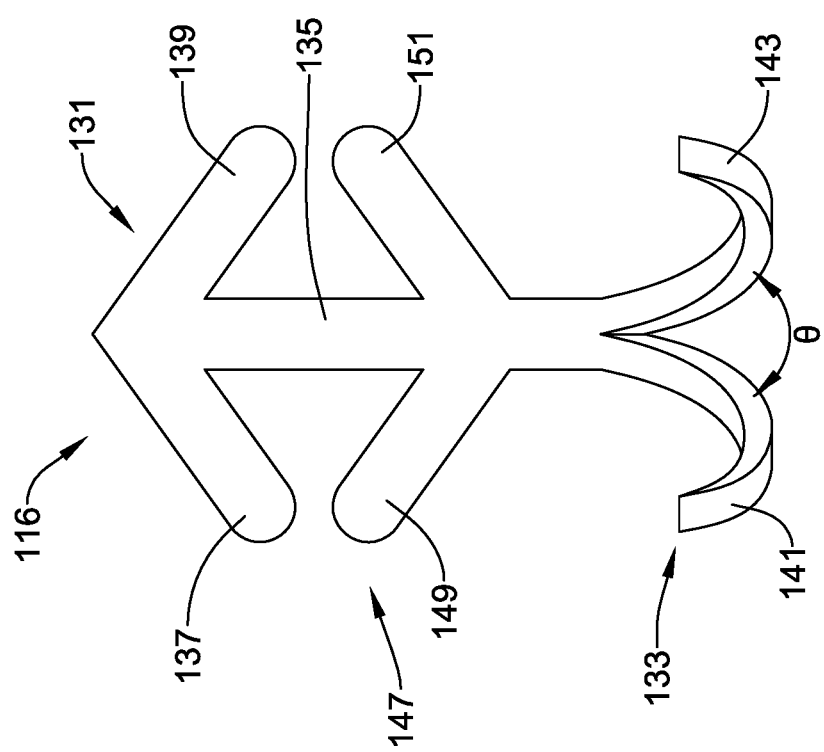
FIG. 7 is a perspective view of the fixation member shown in FIG. 6.

FIG. 7 is a perspective view of the fixation member 116 discussed above with respect to FIG. 6. As described above, FIG. 7 illustrates that the fixation member 116 may include a first engagement portion 131 including the first engagement member 137 and a second engagement member 139. FIG. 7 further illustrates that the fixation member 116 may include the second engagement portion 147 including the third engagement member 149 and the fourth engagement member 151. Additionally, FIG. 7 illustrates that the fixation member 116 may include an anchoring portion 133 which includes the first projection 141 and the second projection 143. Further, FIG. 7 illustrates the medial portion 135 extending between the first engagement portion 131, the second engagement portion 149 and the anchoring portion 133.

Similar to that discussed with respect to the fixation member 16 shown in FIG. 4, the first projection 141 and/or the second projection 143 may include a curved portion which extends the distal ends of the first projection 141 and the second projection 143 outward from the medial portion 135 of the fixation member 116. For example, FIG. 7 illustrates the first projection 141 and the second projection 143 extending outward from the plane of the paper. Additionally, FIG. 7 illustrates that the first projection 141 may be separated from the second projection 143. In other words, FIG. 7 illustrates that the first projection 141 and the second projection 143 may be separated from one another by an angle "θ."

Figure 8:
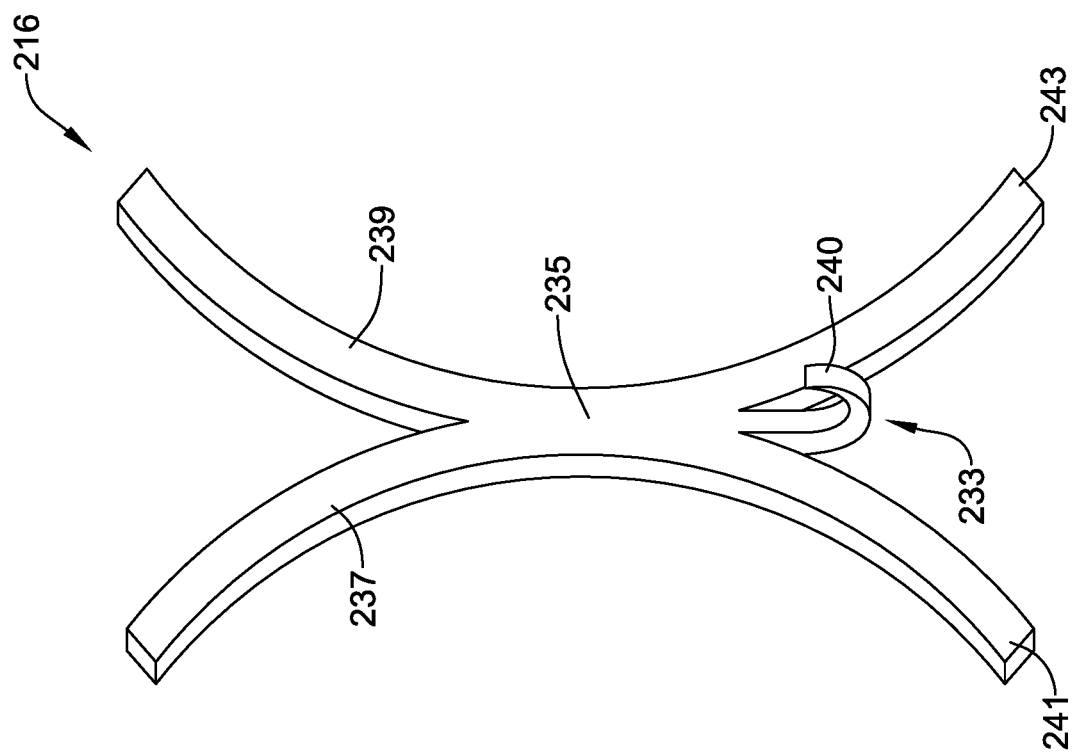
FIG. 8 illustrates another example fixation member.

FIG. 8 illustrates another example fixation member 216. The fixation member 216 may be similar in form and function to other example fixation members described herein. As illustrated in FIG. 8, the fixation member 216 may include a first engagement member 237, a second engagement member 239 a third engagement member 241 and a fourth engagement member 243. The first engagement member 237, the second engagement member 239, the third engagement member 241 and the fourth engagement member 243 may all be positioned adjacent to and/or coupled to a body portion 235 of the fixation member 216. Similar to other fixation members disclosed herein, the first engagement member 237, the second engagement member 239, the third engagement member 241 and/or the fourth engagement member 243 may be designed such that they engage one or more structural members (e.g., one or more filaments) of an expandable member of an occlusive device. For example, the first engagement member 237, the second engagement member 239, the third engagement member 241 and the fourth engagement member 243 may be designed to interlace with one or more filaments of an expandable member of an occlusive device, whereby interlacing with the filaments releasably couples the fixation member 216 to the occlusive device.

FIG. 8 further illustrates that the fixation member 216 may include an anchoring portion 233 extending away from the body portion 235. The anchoring portion 233 may include a projection 240 (e.g., barb, etc.) which may be designed to pierce into tissue at a target site, thereby securing the position of the occlusive device adjacent to the target site (e.g., the left atrial appendage).

Figure 9:
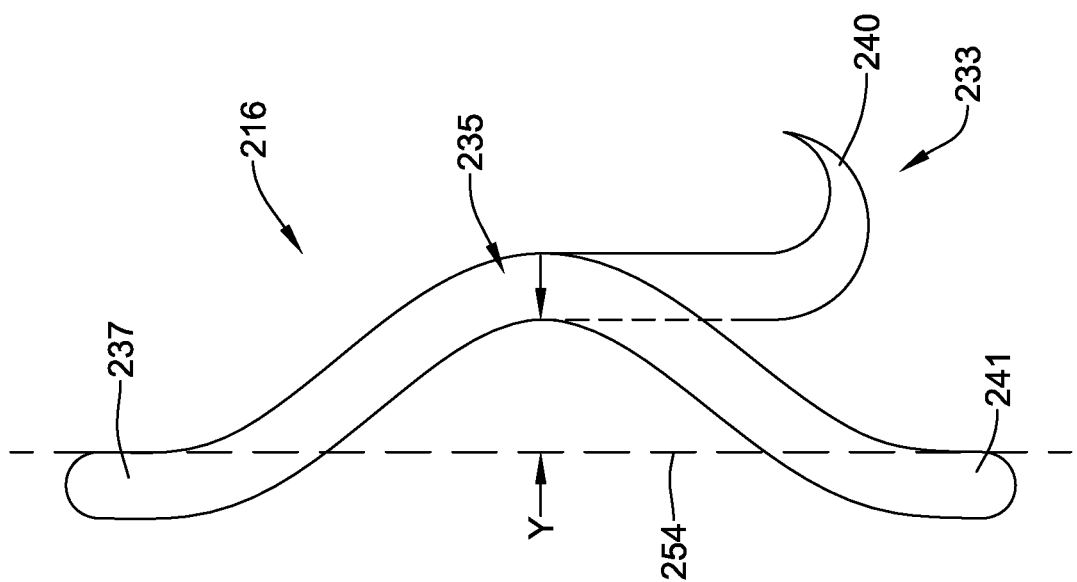
FIG. 9 is a side view of the fixation member shown in FIG. 7.

FIG. 9 is a side view of the fixation member 216 discussed above. FIG. 9 illustrates that, in some examples, the body portion 235 of the fixation device 216 may extend radially outward a relative to the distal end regions of the first engagement member 237, the second engagement member 239 (hidden by the first engagement member 237 and, therefore, not visible in FIG. 9), the third engagement member 241 and/or the fourth engagement member 243 (hidden by the first third member 241 and, therefore, not visible in FIG. 9). For example, FIG. 9 shows a dashed line 254 which may represent the outer surface of an expandable member of an occlusive device. Further, FIG. 9 illustrates that the distal end regions of the first engagement member 237, the second engagement member 239 (hidden by the first engagement member 237 and, therefore, not visible in FIG. 9), the third engagement member 241 and/or the fourth engagement member 243 (hidden by the third engagement member 241 and, therefore, not visible in FIG. 9), may extend inward of the outer surface of an expandable member (e.g., represented by the dashed line 254), and whereby the body portion 235 may extend a distance "Y" radially away from the outer surface 254 of the expandable member. It can be appreciated that extending the body portion 235 away from the outer surface 254 of the expandable member may position the projection 240 of the anchoring portion 233 closer to target tissue of the left atrial appendage.

Figure 10:
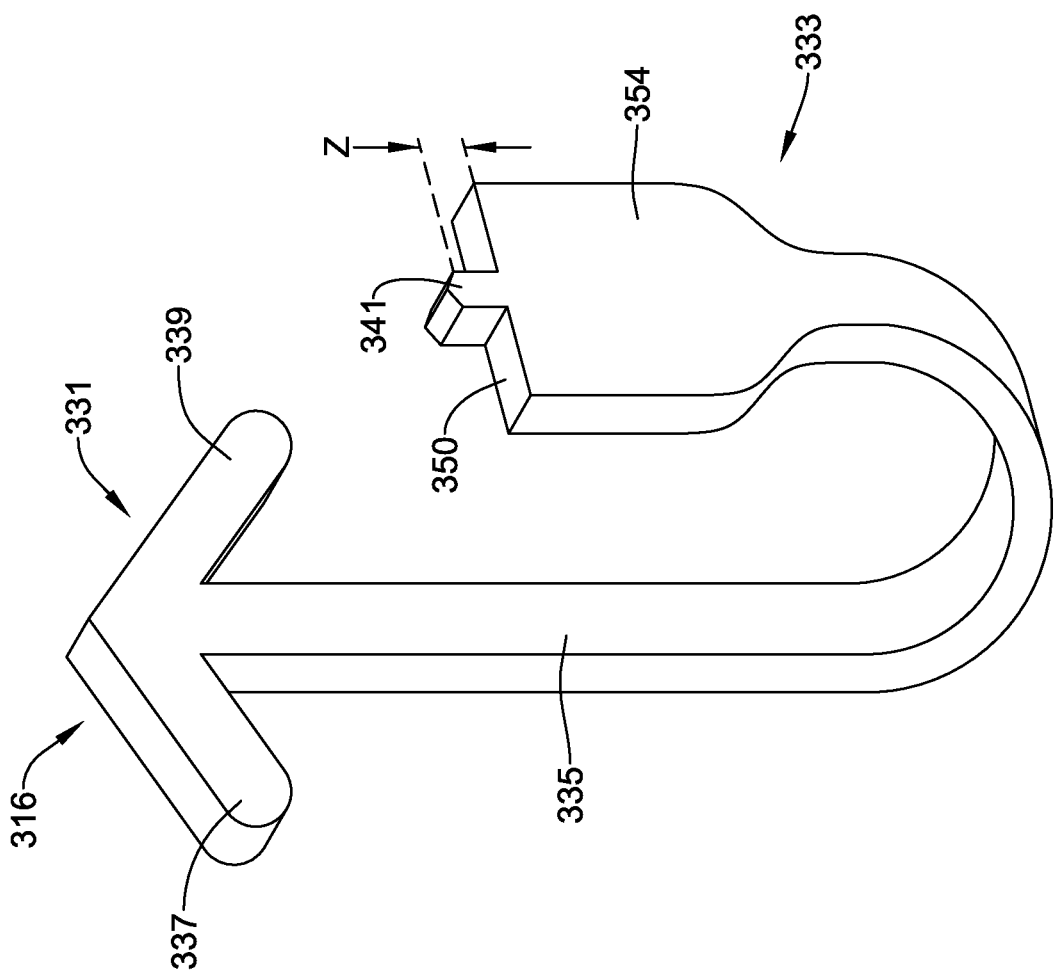
FIG. 10 illustrates another example fixation member.

FIG. 10 illustrates another example fixation member 316. The fixation member 316 may be similar in form and function to other fixation members described herein. For example, the fixation member 316 may include an engagement portion 331 including a first engagement member 337 and a second engagement member 339, whereby the first engagement member 337 and the second engagement member 339 may be utilized to releasably couple the fixation member 316 to one or more structural members (e.g., filaments) of an occlusive device.

Additionally, FIG. 10 illustrates that the fixation member 316 may include an anchoring portion 333 and a medial portion 335 extending between the engagement member 331 and the anchoring portion 333. Further, the anchoring portion 333 may include a projection 341 (e.g., barb, etc.) which may be designed to pierce into tissue at a target site, thereby securing the position of the occlusive device adjacent to the target site (e.g., the left atrial appendage). Further yet, the projection 341 may be coupled to and/or extend away from a base member 354. The base member 354 may include one or more ledges 350 which extend along the distal end of the base member 354.

FIG. 10 further illustrates that the projection 341 may extend a distance "Z" away from the ledges 350 extending along the distal end of the base member 354. It can be appreciated that the ledges 350 may be designed to prevent the projection 341 from extending further than the distance "Z" into target tissue of a target site. For example, the projection 341 may advance into target tissue until the ledges 350 contact the target tissue, thereby preventing the projection 341 from further advancement into the target tissue. In other words, the ledges 350 may act as a positive stop to prevent the projection 341 from extending greater than the distance "Z" into the target tissue.

Figure 11:
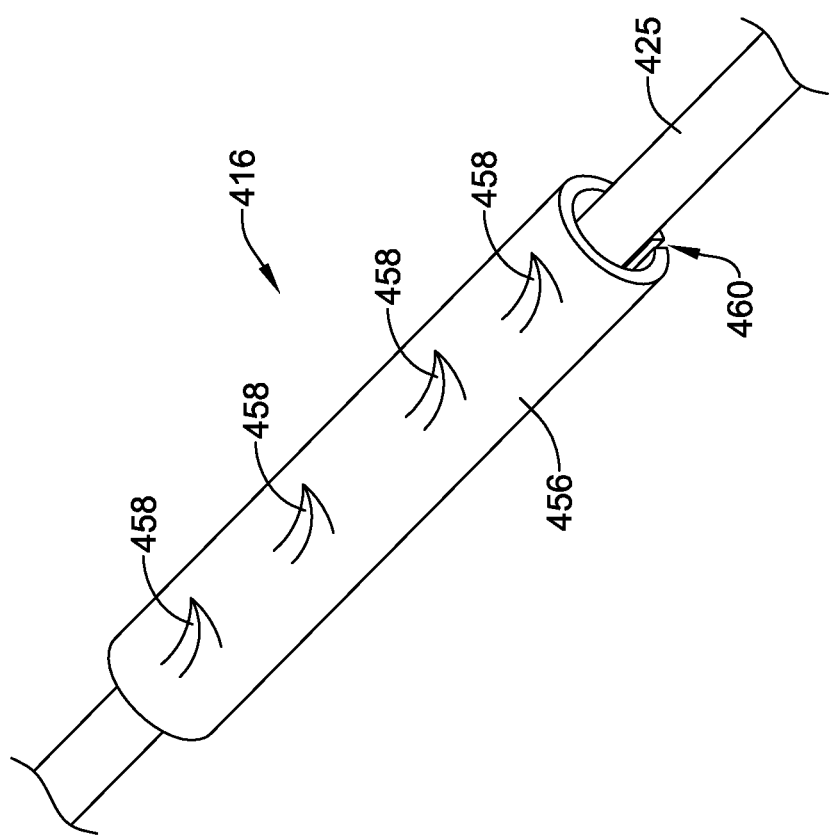
FIG. 11 illustrates an example fixation member disposed along an occlusive implant.

FIG. 11 illustrates another example fixation member 416. The fixation member 416 may include a tubular support member 456. The tubular support member 456 may include a slit 460 which extends along the length of the support member 456. It can be appreciated that the slit 460 may permit the support member 456 to wrap around a portion of an expandable framework of an occlusive device. For example, FIG. 11 illustrates the support member 456 releasably wrapped around a portion of an example filament 425 of an expandable framework of an occlusive device. Similar to other fixation members described herein, the design of the fixation member 416 may permit it to be secured to an occlusive device as an additional manufacturing step distinct from the manufacturing of the occlusive device.

FIG. 11 further illustrates that the fixation member 416 may be designed to include one or more projections 458 extending away from an outer surface of the support member 456. Each of the projections may include a hook, barb, etc. which may be designed to pierce into tissue at a target site, thereby securing an occlusive device (to which the fixation member 416 may be attached) adjacent to the target site (e.g., the left atrial appendage).

Figure 12:
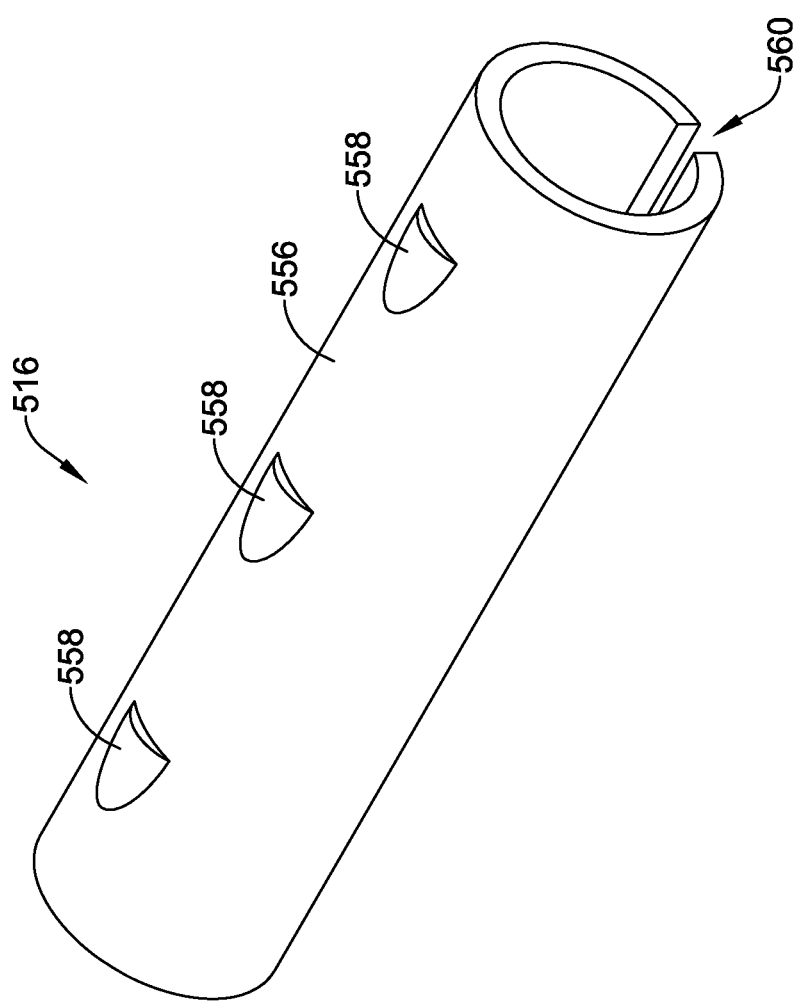
FIG. 12 illustrates an example fixation member disposed along an occlusive implant.

FIG. 12 illustrates another example fixation member 516. The fixation member 516 may include a tubular support member 556. The tubular support member 556 may include a slit 560 which extends along the length of the support member 556. Similar to that described above with respect to FIG. 11, it can be appreciated that the slit 560 may permit the support member 556 to wrap around a portion of an expandable framework, thereby releasably coupling the fixation member 516 to an occlusive device. Similar to other fixation members described herein, the design of the fixation member 516 may permit it to be coupled to an occlusive device as an additional manufacturing step distinct from the manufacturing of the occlusive device.

FIG. 12 further illustrates that the fixation member 516 may be designed to include one or more projections 558 extending away from an outer surface of the support member 556. Each of the projections may include arced portion extending outward from the surface of the support member 556. The projections 558 may be designed to pierce into and/or grip tissue at a target site, thereby securing an occlusive device (to which the fixation member 516 may be attached) adjacent to the target site (e.g., the left atrial appendage).

Figure 13:
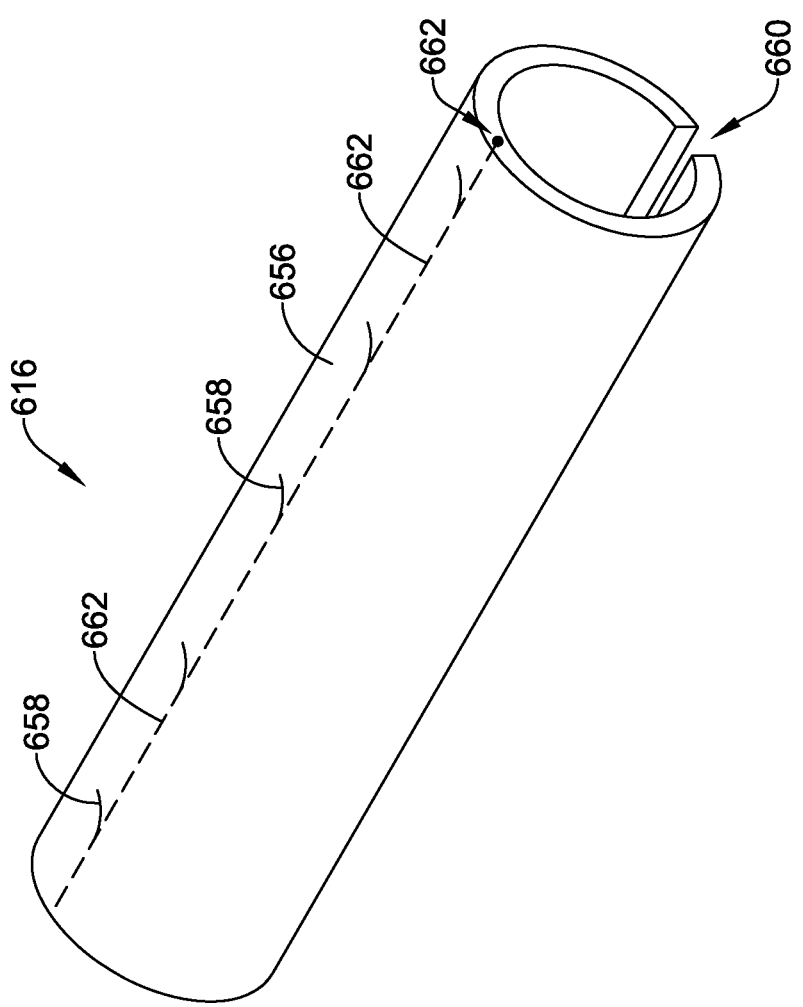
FIG. 13 illustrates an example fixation member disposed along an occlusive implant.

FIG. 13 illustrates another example fixation member 616. The fixation member 616 may include a tubular support member 656. The tubular support member 656 may include a slit 660 which extends along the length of the support member 656. Similar to that described above with respect to FIGS. 11-12, it can be appreciated that the slit 660 may permit the support member 656 to wrap around a portion of an expandable framework, thereby releasably coupling the fixation member 616 to an occlusive device. Similar to other fixation members described herein, the design of the fixation member 616 may permit it to be coupled to an occlusive device as an additional manufacturing step distinct from the manufacturing of the occlusive device.

FIG. 13 further illustrates that the fixation member 616 may be designed to include a wire member 662 positioned within a wall of the support member 656. The wire member 662 may extend along the entire length of (or, alternatively, along only a portion of) the support member 656. Additionally, in some examples, a portion of the wire member 662 may extend radially outward through the wall and away from the outer surface of the support member 656. As shown in FIG. 13, the portion of the wire 662 extending away from the outer surface of the support member 656 may include a hook, barb, etc. 658 which may be designed to pierce into tissue at a target site, thereby securing an occlusive device (to which the fixation member 616 is attached) to the target site (e.g., the left atrial appendage).

Figure 14:
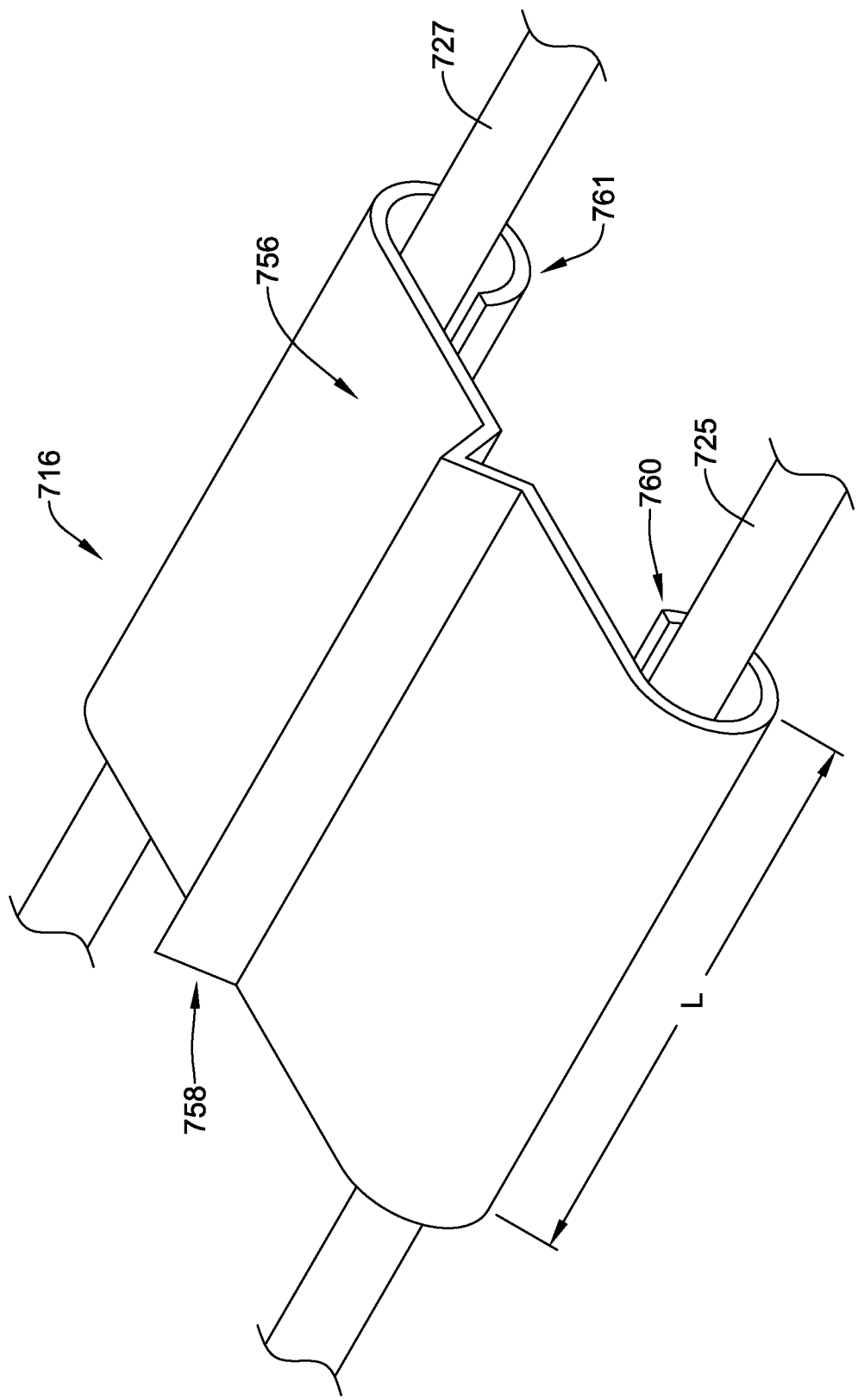
FIG. 14 illustrates an example fixation member disposed along an occlusive implant.

FIG. 14 illustrates another example fixation member 716. As illustrated in FIG. 14, the fixation member 716 may be designed such that it may be secured to two structural members of an occlusion device. It can be appreciated that the first filament 725 and the second filament 727 shown in FIG. 14 may represent two distinct filaments of an expandable member of an occlusion device. In other words, the fixation member 716 shown in FIG. 14 may be designed such that it spans (e.g., extends between) two distinct filaments of an example occlusion device.

FIG. 14 further illustrates that the fixation member 716 may include a base portion 756 having a first lateral side 760 which is secured to a first filament 725 and a second lateral side 761 which is secured to a second filament 727. As shown in FIG. 14, each of the first lateral side 760 and the second lateral side 761 may include a curved portion which is designed to wrap (e.g., curl, snap, affix, press-fit, etc.) around each of the first filament 725 and/or the second filament 727, respectively.

Additionally, FIG. 14 illustrates that the base portion 756 may extend along the first filament 725 and the second filament 727 a length "L". In some examples, the base portion may include a flat sheet-like material, a foil, or the like. It is noted that while FIG. 14 illustrates that the shape of the base portion 756 may be substantially rectangular, other shapes are contemplated. For example, the base portion 756 may include square, triangle, polygon, round, oval or other similarly-shaped portions. Additionally, the base portion 756 may be designed to include any shape necessary to fit within a space defined by one or more filaments utilized to form an expandable member.

Additionally, FIG. 14 illustrates that the fixation member 716 may include a projection 758 extending along the length "L" of the base portion 756. The projection 758 may be designed to engage tissue at a target site, thereby securing an occlusive device to the target site (e.g., the left atrial appendage). While FIG. 14 illustrates the projection 758 including a sharp point, other shapes are contemplated. For example, the projection may include arcs, multiple projections, barbs, hooks, curves, etc.

In some instances, it may be desirable to design the fixation member 716 to shift from a first retracted configuration to an extended configuration. For example, it may be desirable to design the fixation member 716 to shift from a retracted configuration when the expandable member is in a collapsed configuration to an extended configuration when the expandable member is in an expanded configuration. This design feature may be beneficial as it may permit an occlusive device to be collapsed in a reduced profile for delivery via a delivery system, yet would also permit the projection 758 to anchor the occlusive device to target tissue upon deployment (e.g., expansion) of the occlusive device.

Figure 15:
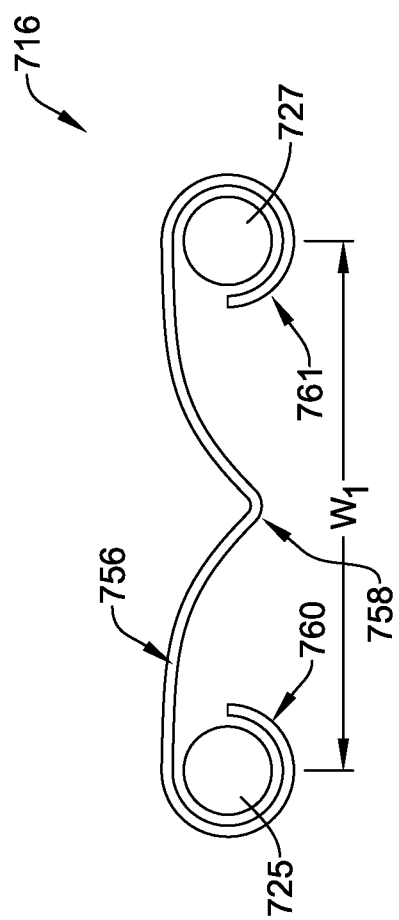
FIG. 15 illustrates an end view of the fixation member shown in FIG. 14 in a retracted configuration.
Figure 16:
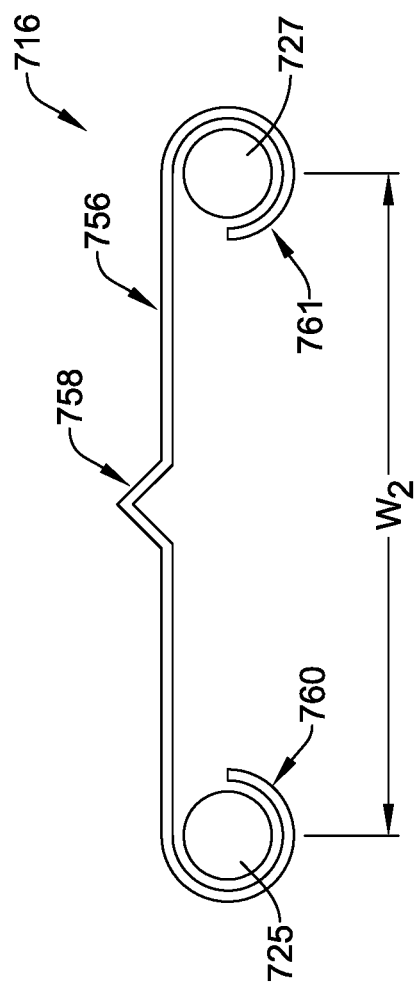
FIG. 16 illustrates an end view of the fixation member shown in FIG. 14 in an extended configuration.

FIG. 15 and FIG. 16 illustrate the fixation device 716 shifting from a retracted configuration to an extended configuration. For simplicity purposes, it can be appreciated that FIG. 15 may represent a portion of an occlusive device in collapsed configuration, whereby the fixation member 716 is retracted radially inward and that FIG. 16 may represent the occlusive device in an expanded configuration, whereby the fixation member 716 is extended radially outward. It can further be appreciated that first filament 725 and the second filament 727 may be separated a distance "$W_1$" in the retracted (e.g., collapsed) configuration (illustrated in FIG. 15), and that the first filament 725 and the second filament 727 may be separated a distance "$W_2$" in the extended (e.g., expanded) configuration (illustrated in FIG. 16). It can be appreciated that the distance $W_1$ may be less than the distance $W_2$. Additionally, FIG. 15 and FIG. 16 illustrate that as the fixation member 756 expands from a collapsed configuration to an expanded configuration, the projection 758 may shift from being oriented radially inward (e.g., pointed away from target tissue) to being oriented radially outward (e.g., pointed toward target tissue). As discussed above, when the projection is oriented radially outward, it may be positioned to engage target tissue.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MRI) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like.

The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant, comprising:
   an expandable framework configured to shift between a first configuration and an expanded configuration; and
   a fixation member disposed along the expandable framework, wherein the fixation member includes a first engagement portion and an anchor portion, wherein the first engagement portion is designed to be secured to the expandable framework, wherein the fixation member includes a first end, a second end opposite the first end and a medial portion extending between the first end and the second end, and wherein the first engagement portion is positioned along the first end of the fixation member and wherein the anchor portion is positioned along the second end of the fixation member, wherein the first engagement portion includes a first engagement member and a second engagement member, wherein both the first engagement member and the second engagement member are offset from the medial portion;

wherein the anchor portion extends away from an outer surface of the expandable framework;

wherein at least a portion of the expandable framework is positioned between the first engagement member and the medial portion and wherein at least a portion of the expandable framework is positioned between the second engagement member and the medial portion;

wherein the fixation member is disposed along the expandable framework such that at least a portion of first engagement member and at least a portion of the second engagement member are positioned along an outer surface of the expandable framework and at least a portion of the medial portion is positioned along an inner surface of the expandable framework.

2. The occlusive implant of claim 1, wherein the first engagement portion is removably secured to the expandable framework.

3. The occlusive implant of claim 1, wherein the first engagement portion is designed to be rigidly secured to the expandable framework.

4. The occlusive member of claim 1, wherein the anchor portion includes a first projection and a second projection, and wherein the second projection is offset from the first projection.

5. The occlusive member of claim 1, wherein the fixation member further comprises a second engagement portion positioned adjacent to the first engagement portion, and wherein the second engagement portion includes a third engagement member and a fourth engagement member.

6. The occlusive member of claim 5, wherein the fixation member is disposed along the expandable framework such that at least a portion of third engagement member and at least a portion of the fourth engagement member are positioned along the outer surface of the expandable framework and at least a portion of the medial portion is positioned along the inner surface of the expandable framework.

7. The occlusive member of claim 6, wherein at least one of the first engagement member, the second engagement member, the third engagement member and the fourth engagement member are interlaced with a least a portion of the expandable framework.

8. An occlusive implant, comprising:

an expandable framework configured to shift between a first configuration and an expanded configuration; and a fixation member disposed along the expandable framework, wherein the fixation member includes a first engagement portion and an anchor portion, wherein the first engagement portion is designed to be secured to the expandable framework, wherein the fixation member includes a first end, a second end opposite the first end and a medial portion extending between the first end and the second end, and wherein the first engagement portion is positioned along the first end of the fixation member and wherein the anchor portion is positioned along the second end of the fixation member, wherein the first engagement portion includes a first engagement member and a second engagement member, wherein both the first engagement member and the second engagement member are offset from the medial portion;

wherein the anchor portion extends away from an outer surface of the expandable framework;

wherein the expandable framework includes a first filament interwoven with a second filament, and wherein the first filament crosses the second filament at an intersection point, and wherein the fixation member is positioned adjacent to the intersection point.

9. The occlusive member of claim 8, wherein the first filament is positioned between the first engagement member and the medial portion, and wherein the second filament is positioned between the second engagement member and the medial portion.

10. An occlusive member, comprising an expandable framework configured to shift between a first configuration and an expanded configuration; and a fixation member disposed along the expandable framework, wherein the fixation member includes a first engagement portion and an anchor portion, wherein the first engagement portion is designed to be secured to the expandable framework;

wherein the anchor portion extends away from an outer surface of the expandable framework, wherein the anchor portion includes a first projection and a second projection, and wherein the second projection is offset from the first projection;

wherein each of the first projection and the second projection includes an arcuate portion.

* * * * *